United States Patent [19]

Small

[11] 4,127,611

[45] Nov. 28, 1978

[54] PROCESS FOR THE REDUCTIVE METHYLATION OF AN ACID HYDRAZIDE

[75] Inventor: Robert J. Small, Worthington, Ohio

[73] Assignee: Ashland Oil, Inc., Ashland, Ky.

[21] Appl. No.: 840,538

[22] Filed: Oct. 11, 1977

[51] Int. Cl.² .............................................. C07C 85/00
[52] U.S. Cl. .............................. 260/583 B; 260/561 H
[58] Field of Search ........................ 260/583 B, 561 H

[56] References Cited

U.S. PATENT DOCUMENTS

| 2,589,290 | 3/1952 | Sampson | 260/561 H X |
|---|---|---|---|
| 3,296,307 | 1/1967 | MacGregor et al. | 260/583 B |
| 3,965,174 | 6/1976 | Malz, Jr. et al. | 260/561 H |
| 4,045,484 | 8/1977 | Malz, Jr. et al. | 260/561 H |

FOREIGN PATENT DOCUMENTS 554,850  2/1957  Belgium ............................... 260/583 B

*Primary Examiner*—Allen B. Curtis

[57] ABSTRACT

A residual amount of hydrazine present in an acethydrazide solution prepared by condensing hydrazine with ethyl acetate is treated by either reaction with carbon dioxide or oxidation with air in the presence of palladium or platinum catalyst. Treatment of said acid hydrazide solution in the foregoing manner obviates the catalyst poisoning potential of the unreacted hydrazine upon subsequent reductive methylation of the hydrazide solution in the presence of palladium or platinum catalyst.

1 Claim, No Drawings

PROCESS FOR THE REDUCTIVE METHYLATION OF AN ACID HYDRAZIDE

BACKGROUND OF THE INVENTION

1. Field of the Invention

This invention relates to a process for the catalytic reductive methylation of an acid hydrazide wherein the latter is pretreated to eliminate catalyst poisoning contaminants.

2. Description of the Prior Art

Mono methyl hydrazine (MMH) and unsymmetrical dimethyl hydrazine (UDMH), due to the ability of these compounds to provide hypergolic ignition upon contact with a strong oxidizer, represent important liquid propellant fuels, particularly for space vehicles. Although there are several routes available for the commercial production of these compounds, all, however, involve problems of one type or another.

For example, the most expedient process for producing UDMH consists of hydrogenating nitrosodimethylamine in turn obtained by nitrosating dimethylamine. This process, however, has been banned for all practical purposes because of the extremely potent carcinogenic nature of the nitrosodimethylamine intermediate. A currently practiced process for producing MMH is in accordance with a modified Raschig synthesis involving the in situ generation of mono-chloramine and subsequent reaction with monomethyl amine. The principal disadvantage of this process is that it is excessively energy intensive.

A hitherto proposed process commercially applicable for producing UDMH as well as MMH, and the process to which the present invention relates, consists of the reductive alkylation of an acid hydrazide with formaldehyde in the presence of hydrogen and a suitable hydrogenation catalyst and subsequent base hydrolysis or hydrozinolysis of the resultant alkylate.

The most effective catalyst for this purpose is either platinum or palladium, preferably the latter supported on carbon. In accordance with the process, optimum yield of UDMH, and likewise MMH, is in the order of 80–85%. In order to realize such a yield, however, it is necessary to take the necessary precautions to avoid the poisoning of the catalyst during the course of the reaction.

Free hydrazine present in the reaction mixture, even in the amount of one percent or less, can have a very deleterious effect on catalyst activity. Although the preferred procedure for preparing the acid hydrazide intermediate involves the use of a substantial deficiency of the hydrazine, an unreacted amount thereof in the order mentioned is invariably present. A suitable way of eliminating free hydrazine is to adjust the pH of the hydrazine solution to neutral or slightly on the acid side with acetic acid or like acids or anhydrides. However, these acids contribute to overall cost, are corrosive and consume caustic in the hydrolysis reaction. It is, accordingly, the object of this invention to provide an alternative way for eliminating the free hydrazine present in an acid hydrazine prepared in the manner indicated without resort to the use of an acid as aforesaid.

SUMMARY OF THE INVENTION

In accordance with the present invention, an acethydrazide solution obtained by condensing hydrazine with a stoichiometrical excess of ethyl acetate is pretreated so as to convert free residual hydrazine to a form devoid of catalyst poisoning effects upon subsequent catalytic reductive alkylation of the acid hydrazide. The pretreatment method contemplated involves two different but functionally equivalent procedures. In one mode, the hydrazide solution is intimately contacted with carbon dioxide. In the alternative mode, the acid hydrazide is contacted with oxygen or a free oxygen containing gas in the presence of catalytically active palladium or platinum.

DESCRIPTION OF THE PREFERRED EMBODIMENTS

For the purpose of describing the implementation of the present invention, such will be illustrated in context of the process for preparing UDMH wherein acethydrazide is reacted with formaldehyde in the molar ratio of about 1:2, respectively, under a hydrogen atmosphere and in the presence of palladium on carbon catalyst. This process, as well as the preparation of the starting acethydrazide solution for treatment in accordance with this invention, will be adequately exemplified in the working examples to follow. Further details concerning the reductive methylation reaction and the attendant hydrolysis procedure employed herein can be found in Belgian Pat. No. 839,664.

In the following examples, all parts and percentages given are by weight unless otherwise indicated.

EXAMPLE I

A stock solution of acethydrazide was prepared by charging to a suitable reaction vessel 2331 g. of ethyl acetate and 1421 g. of 85% hydrogen hydrate (54.5% hydrazine). With stirring, the reaction mixture was heated to about 60° C. and held for 70 hours. The resultant hydrazide solution analyzed less than 1% free hydrazine and exhibited of pH of 8.9.

Carbon dioxide was bubbled through 474 g. of the above hydrazide solution for about one hour resulting in a decrease of pH to 6.6. The treated solution was then charged to a pressure vessel along with 11.2 of Pd/C catalyst (50% wet) and the reactor sealed and heated to 83° C. Methyl Formcel in the amount of 350 g. containing 9 g. of acetic acid was pumped into the reactor over a 77 minute period while maintaining a hydrogen pressure of 155 psig. The reaction mixture was pressure filtered and stripped to yield 316 g. of a water-white liquid.

A 1.5 mole aliquot portion of the alkylated product was hydrolyzed with a 100% excess of 50% aqueous sodium hydrazide. Hydrolysis provided a total yield of UDMH of 84%.

EXAMPLE II

A stock solution of acethydrazide was prepared employing the reactant ratios specified in Example I. The reaction mixture was heated to 70° C. and held for about 18 hours with stirring. The pH of the final product was 9.2. To a suitable pressure reaction vessel was charged 317 g. of the above stock hydrazide solution followed by the addition of 7.5 g. of Pd/C catalyst (50% wet). Air was sparged through the mixture of catalyst and the hydrazide solution for approximately 90 minutes. THe final pH of the hydrazide solution was 6.5.

The reactor was sealed and the hydrazide solution heated to 86° C. Methyl Formcel in the amount of 233 g. containing 5.7 g. acetic acid was pumped into the reactor over a 50 minute period while maintaining a hydrogen pressure of 155 psig. The reaction product was pressure filtered and stripped to yield 205 g. of a water-white liquid.

A 1.5 mole aliquot portion was hydrolyzed with a 100% excess of 50% aqueous sodium hydrazide. Total yield of UDMH was 85%. By-products consisted of 0.35 litre of non-condensable gas and 0.4 g. of dry ice condensable gases. What is claimed is:

1. In a process for the reductive methylation of acethydrazide wherein a solution of said hydrazide prepared by condensing hydrazine or an aqueous solution thereof with a stoichiometrical excess of ethyl acetate is reacted with formaldehyde in the presence of hydrogen and palladium or platinum catalyst supported on carbon; the improvement of pretreating the resultant hydrazide solution to effect removal of residual catalyst poisoning amounts of hydrazine which alternatively consists of either:

(a) contacting the hydrazide solution with carbon dioxide until the solution exhibits a pH not in excess of 7.0; or (b) charging the requisite amount of catalyst for effecting said reductive methylation reaction to the hydrazide solution and thereupon contacting the solution with air until same exhibits a pH not in excess of 7.0.

* * * * *